US010321857B2

(12) United States Patent
Stevens et al.

(10) Patent No.: US 10,321,857 B2
(45) Date of Patent: Jun. 18, 2019

(54) FIELD-OF-VIEW OCULAR AND FACIAL ALIGNMENT GUIDES

(71) Applicant: INTEL CORPORATION, Santa Clara, CA (US)

(72) Inventors: Kerry A. Stevens, Beaverton, OR (US); Yoshifumi Nishi, Aloha, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 15/607,312

(22) Filed: May 26, 2017

(65) Prior Publication Data

US 2017/0258371 A1  Sep. 14, 2017

Related U.S. Application Data

(62) Division of application No. 14/752,939, filed on Jun. 27, 2015, now Pat. No. 10,117,603.

(51) Int. Cl.
*G06K 9/00* (2006.01)
*A61B 5/117* (2016.01)
*G06F 21/32* (2013.01)
*G06F 21/83* (2013.01)

(52) U.S. Cl.
CPC .............. *A61B 5/117* (2013.01); *G06F 21/32* (2013.01); *G06F 21/83* (2013.01); *G06K 9/00597* (2013.01)

(58) Field of Classification Search
CPC ......... A61B 3/1225; A61B 3/12; A61B 3/103; A61B 3/1015; A61B 3/0008
USPC .................................................. 351/221, 246
See application file for complete search history.

(56) References Cited

U.S. PATENT DOCUMENTS

| 2,185,628 | A |   | 1/1940 | Daum |
| 5,035,500 | A | * | 7/1991 | Rorabaugh ............ A61B 3/024 351/224 |
| 6,604,315 | B1 |   | 8/2003 | Smith et al. |
| 2005/0254151 | A1 |   | 11/2005 | Townsend et al. |
| 2006/0184243 | A1 |   | 8/2006 | Yilmaz |
| 2008/0044063 | A1 | * | 2/2008 | Friedman ............ A61B 3/1216 382/117 |

(Continued)

FOREIGN PATENT DOCUMENTS

EP  1491141 A2  12/2004

OTHER PUBLICATIONS

Final Office Action dated Dec. 7, 2017, issued in related U.S. Appl. No. 14/752,939, 13 pages.

(Continued)

*Primary Examiner* — James R Greece
(74) *Attorney, Agent, or Firm* — Schwabe, Williamson & Wyatt, P.C.

(57) ABSTRACT

Low-cost, easy-to-use alignment target generators for aligning a user's own face or eye to a camera or scanner are based on field-of-view visual feedback from a filtered or apertured planar light source. These approaches may be made agnostic to the scanner's operating system or other software. Alternatively, software on the scanner or its host device may create a solid light-colored section of an existing display screen to use as a planar light source. In some embodiments, the planar light source may be the virtual image of an object viewed in a plane mirror.

9 Claims, 8 Drawing Sheets

(56) References Cited

U.S. PATENT DOCUMENTS

| | | |
|---|---|---|
| 2009/0147358 A1 | 6/2009 | Charlesworth |
| 2011/0285825 A1 | 11/2011 | Tian et al. |
| 2012/0062998 A1 | 3/2012 | Schultz et al. |
| 2012/0075168 A1 | 3/2012 | Osterhout et al. |
| 2014/0193046 A1 | 7/2014 | Mason et al. |
| 2016/0291326 A1 | 10/2016 | Evans et al. |

OTHER PUBLICATIONS

Non-Final Office Action dated Jul. 3, 2017, issued in related U.S. Appl. No. 14/752,939, 14 pages.
International Search Report and Written Opinion dated Dec. 20, 2016, issued in related International Application No. PCT/US2016/039683, 13 pages.
Extended European Search Report dated Jan. 2, 2019 for European Patent Application No. 16818563.5, 7 pages.

* cited by examiner

FIELD-OF-VIEW OCULAR AND FACIAL ALIGNMENT GUIDES

RELATED APPLICATIONS

This application claims the benefit of priority from U.S. Non-Prov. patent application Ser. No. 14/752,939 filed Jun. 27, 2015 which is entirely incorporated by reference herein.

FEDERALLY SPONSORED RESEARCH AND DEVELOPMENT

None

APPENDICES

None

FIELD

Related fields include biometrics, and more particularly facial scanning and recognition.

DETAILED DESCRIPTION

Biometric methods of identification are presently of increasing interest to thwart and deter fraud and identity theft and to make personal portable electronics less valuable to property thieves. Of the desirable properties of an identification biometric trait, iris scanning scores very high in uniqueness, universality, permanence, performance, and (difficulty of) circumvention, and in the midrange of collectability and acceptability. Iris scanning can be sensitive to inconsistencies in distance or angle between the scanner and the user's body. Vignetting, where part of the object being measured is blocked by the apertures in the scanner or by external objects, may be an especially troublesome source of false errors. This sensitivity, and the resulting "stand very still and stare" requirement placed on users. may be a contributing factor keeping the acceptability score low.

For purposes herein, the following terms shall have the following meanings:

"User": A person being identified by a biometric device. One who uses the biometric device to identify others will be called an "operator" for purposes of this document.

"Planar light source": may refer to a direct source of light, such as an LED array, or an indirect source, such as an illuminated diffuser or mirror, in which the light exits from a substantially flat surface (e.g., best-fit radius>1 m; rms roughness<1 mm).

"Scan": may refer to any method of data capture for biometrics of a user's eye or face.

"Optical surface": a surface prepared (e.g. shaped, polished or patterned) for entry and/or exit of light (e.g., in most lenses and filters, the front and the back but not the edge; in most prisms, two or more of the non-parallel sides but not the two parallel sides). Not all optical surfaces are smooth or regularly patterned; for example, diffusers may have optical surfaces with controlled random roughness.

"Parent device": The device that includes the biometric scanner; this may be a dedicated biometric system (e.g., at the door of an employee-only entrance) or a protected device used for other purposes but equipped with a biometric scanner to limit access to itself, A computer or smart-phone, a high-end machine tool, and a household or company safe are non-limiting examples.

Figure 1:
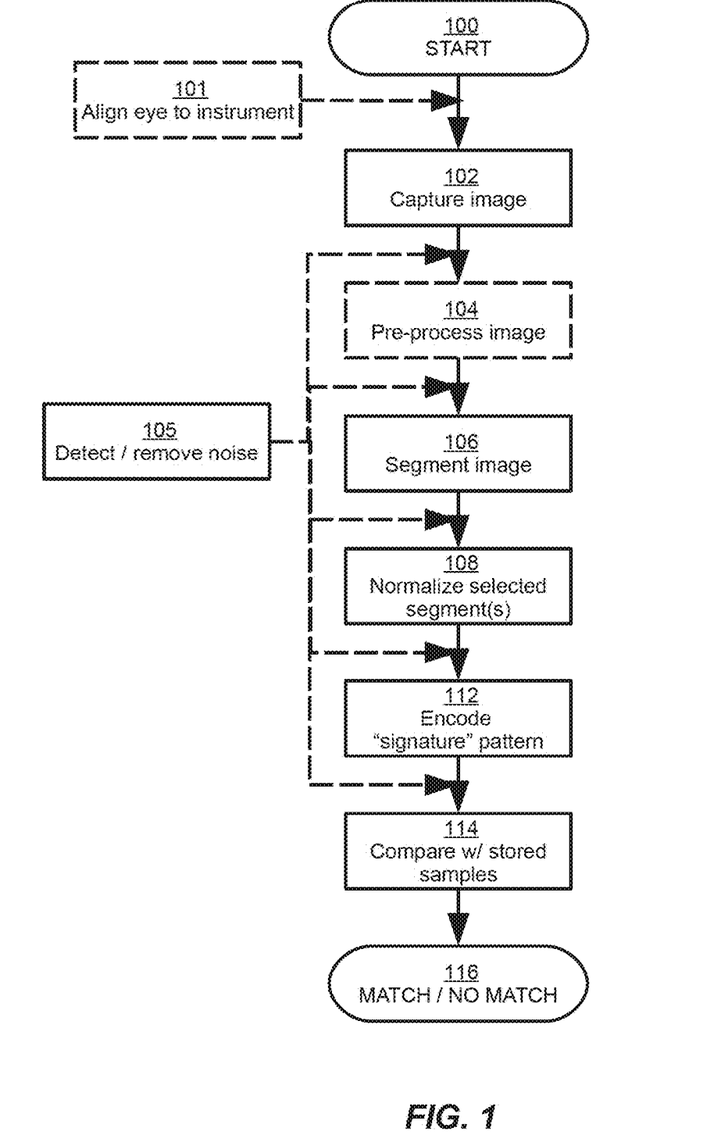
FIG. 1 is a flowchart of an example of a process for iris scanning.

FIG. 1 is a flowchart of an example of a process for iris scanning. Other processes may involve more or fewer steps, or some different steps, yet may be equivalents because they may be similarly sensitive to positioning or angle of a user's eye.

The process may be started at step 100 by a user pushing a button, touching a screen, scanning a card or tag, or being detected approaching and stopping within a detection zone. Alternatively, an official operator, such as a test proctor or border guard, may start the process after having the user move into the detection zone.

An image of the user's iris, or equivalently a stream of data from a spot scan or some other collection of raw data, is captured in step 102. In some systems, the image (or other raw data) may be pre-processed at step 104. For example, the pre-processing may include separating colors to create one or more monochromatic images; separating the iris data from measurements of nearby features such as the sclera, pupil, or eyelid; or accessing a spatial-frequency spectrum from a transform such as a fast Fourier transform (FFT) or a circular Hough transform.

Image segmentation at step 106 often includes edge detection and may use approaches such as gradient amplitude, gamma modification, non-maxima suppression, or hysteresis thresholding. At step 108, the extracted data sets are normalized to simplify comparison with stored records. At step 112, the iris's "signature," including its most unique features, is encoded. Many, if not most, of the features that distinguish one individual iris from another are capable of being encoded at low or low-middle frequencies. Therefore, high-frequency noise can be removed from the data with little risk. Step 105, detecting and removing noise, may optionally be done in its various aspects following image capture 102, pre-processing 104, segmentation 106, normalization 108, or encoding 112. Noise an iris measurement may result from the presence of the users' eyelashes or blood vessels in the field of measurement, as well as potentially being introduced by imperfections in the equipment and process.

At step 114, the encoded signature pattern is compared with stored samples, e.g., by calculating the Hamming distance between the new sample in the stored sample, or by some other suitable algorithm. Finally at step 116, the comparison calculations yield a "match or no match" result.

Step 101, the alignment of the eye to the instrument, continues to be challenging on multiple levels. Including, in the scanner, a dedicated camera just for the pre-scan alignment process may be costly, bulky, or fragile depending on the scanner configuration and its environment of use. Particularly in self-service situations, an affordable, rugged, and easy wait to pre-align the eye before taking the scan has the potential to mitigate users' aversion to complicated or highly constrained processes.

FIGS. 2A-D represent examples of iris vignetting.

Figure 2A:
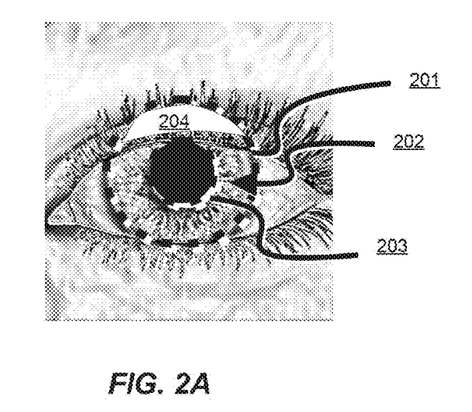
FIGS. 2A-D represent examples of iris vignetting

The iris in FIG. 2A is in its least-vignetted natural position. The eye is fairly centered and its optic axis is substantially parallel to the scanner optic axis, and the head is facing directly toward the scanner. Dotted-line circle 201 marks the outer iris boundary between the iris and the sclera. Similarly, dotted-line circle 203 marks the inner iris boundary between the iris and the pupil. Even in this optimal position, area 204 of the iris is vignetted by the upper eyelid and eyelashes making some of the iris features inaccessible. Area 204 may be enlarged in some instances if the user is wearing mascara, sleepy, or suffering from allergies, conjunctivitis or a similar eye irritation.

Figure 2B:
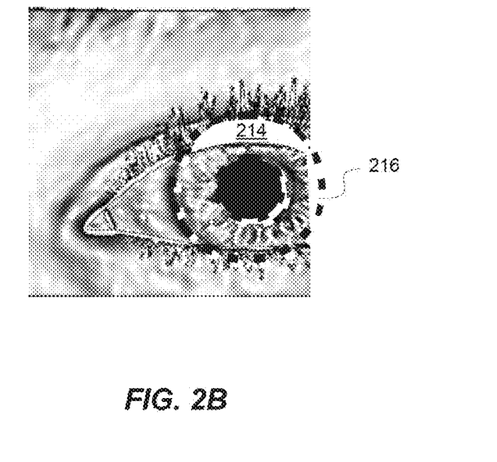

In FIG. 2B, the iris is still centered in the eye and the optic axis of the eye is still parallel to the optic axis of the scanner, but the eye was off-center in the scanner field when the scan was taken. Area 214 of the iris is vignetted by the upper eyelid and eyelashes. Additionally, area 216 outside the scan border is vignetted by the edge of the image-capture field and therefore not readable.

Figure 2C:
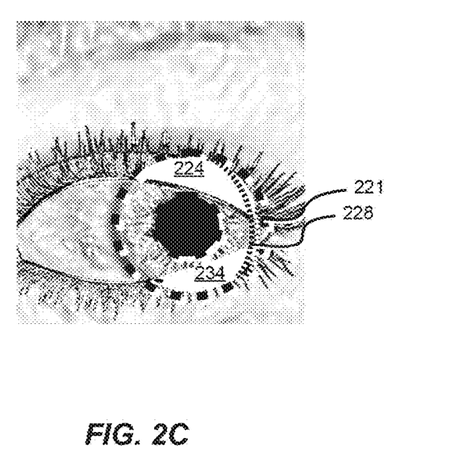

In FIG. 2C, the eye is looking off towards the side and the iris is in the corner of the eye. Area 224 of the iris is vignetted by the upper eyelid and eyelashes. Area 234 of the iris is vignetted by the lower eyelid and eyelashes. Additionally, the iris is distorted by foreshortening due to a non-perpendicular angle between the optic axis of the eye and the optic axis of the scanner. The right edge of the iris is along line 228 rather than 221, which distorts the aspect ratio of iris features.

Figure 2D:
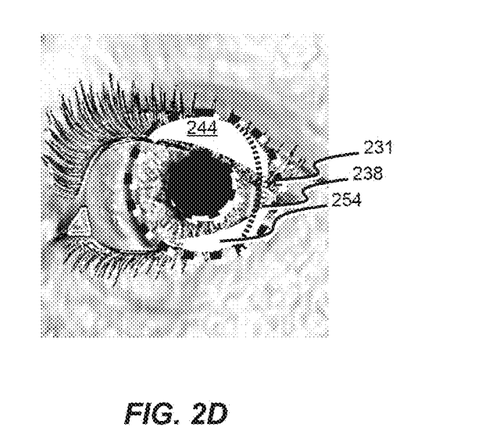

In FIG. 2D, the eye is looking off straight into the scanner but the head is turned partially away from the scanner, again putting the iris in the corner of the eye. Area 244 of the iris is vignetted by the upper eyelid and eyelashes. Area 254 of the iris is vignetted by the lower eyelid and eyelashes. Foreshortening places the iris edge at line 238 instead of line 231.

In FIGS. 2B, 2C and 2D, misalignment of the eye or head to the scanner results in more missing or distorted iris features than the optimal alignment of FIG. 2A. If enough distinguishing features are missing or distorted, the odds of a false match or mismatch increase.

FIGS. 3A-G are conceptual illustrations of examples of planar light sources. The examples are non-limiting; other types of planar light sources besides these may be used with embodiments of alignment target generators.

Figures 3A, 3B:
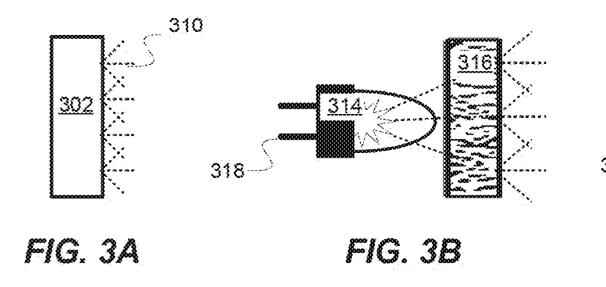
FIGS. 3A-G are conceptual illustrations of examples of planar light sources.

FIG. 3A is a schematic symbol for a planar light source 302 emitting light 310. This symbol in later drawings may represent any of the other illustrated planar light sources or any suitable known substitute.

FIG. 3B represents a light-emitting diode (LED) 314 powered through conductive prongs 318 and illuminating planar diffuser 316. LED 314 may emit light in the manner of a point light source, but when its emitted light is scattered by planar diffuser 316, the front surface of planar diffuser 316 behaves as a planar light source. Although a packaged LED 314 and separately mounted diffuser 316 are illustrated for ease of understanding, any or all of the components may be thin-film components integrated on a chip in some embodiments. Additionally, a reflective diffuser may replace the illustrated transmissive planar diffuser 316 in some embodiments.

Figure 3C:
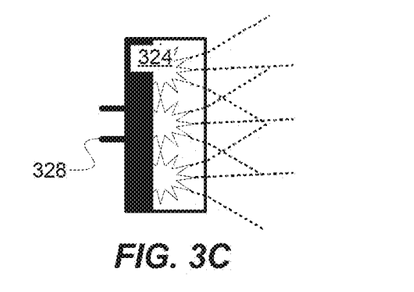

FIG. 3C represents an LED array 324 powered through conductive prongs 318. Individual point-source LEDs are placed sufficiently close together that the human eye sees them as a planar (or linear) light source. A packaged LED array 324 is illustrated for ease of understanding, but LED array 324 may alternatively be integrated on a chip with other scanner components in some embodiments.

Figure 3D:
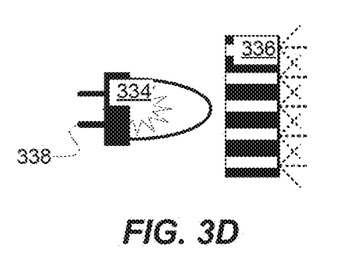

FIG. 3D represents an LED 334 powered through conductive prongs 338 and illuminating light-guide array 336. LED 334 may behave essentially like a point light source, but when its light is captured and reshaped by light-guide array 336, the front surface of light-guide array 336 behaves as a planar light source. Light-guide array 336 may be an array of integrated-optics light-guides or a rigid or flexible bundle of optical fibers. Light-guide array 336 may be short or long. The light guides in light-guide array 336 may be step-index, graded-index, single-mode, multimode or reflective tubes. Although a packaged LED 334 and separately mounted light-guide array 336 are illustrated for ease of understanding, any or all of the components may be thin-film components integrated on a chip in some embodiments.

Figure 3E:
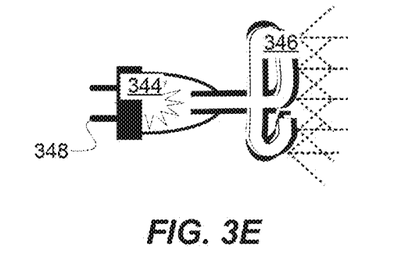

FIG. 3E represents an LED 344 powered through conductive prongs 348 and illuminating edge-emitting optical fiber 346. LED 344 may behave essentially like a point light source, but when its light is captured and reshaped by edge-emitting optical fiber 346, the front surface of a coil or other planar formation of edge-emitting optical fiber 346 behaves as a planar light source. Although a packaged LED 334 and coupled edge-emitting optical fiber 346 are illustrated for ease of understanding, any or all of the components may be thin-film components integrated on a chip in some embodiments.

Another alternative family of embodiments may use an existing visible LED on the parent device that can be caused to stay on when the alignment target generator is being used (e.g., "Power On" or "Caps/Num/Fn Lock"). A permanent or removable light-spreading element such as diffuser 316, light-guide array 336, or edge-emitting fiber 346 can be positioned in front of the existing LED to form a planar light source.

Figure 3F:
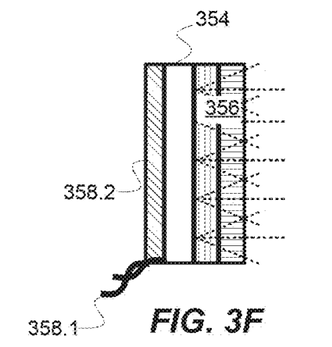

FIG. 3F represents a self-illuminating screen 354; for example, based on LEDs or liquid-crystal diodes. Self-illuminating screen 354 is shown as powered through conductive leads 358.1 and back electrode 358.2, but may equivalently use a transparent front electrode, or both. Light-emitting layer 354 emits the light from individual pixels or LED illumination divided into pixels. Light-altering layer(s) 356 (polarizers, filters, microlenses, etc.) may be added to change the character of the emitted light.

Self-illuminating screen 354 may have all its pixels emitting one color, such as white, or may have adjacent pixels emitting different colors for the appearance of a solid mixed color. The resolution may be fairly low and self-illuminating screen 354 will still appear as a planar light source to the user's eye.

In some embodiments, self-illuminating screen 354 may be a section of a larger screen, such as a display screen for a smart-phone, tablet computer, or personal computer that authenticates its users through iris recognition.

Figure 3G:
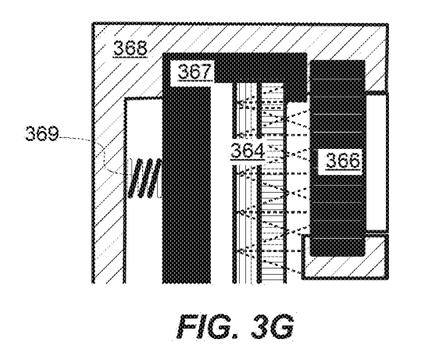

In FIG. 3G, self-illuminating screen 364 is a larger display screen mounted in housing 367. To perform the iris scan, optics train 366 may be temporarily mounted over part of self-illuminating screen 364 and its housing 367 by removable mounting clip 368. Removable mounting clip 368 may be held in place by a spring force 369, by friction between an inner surface of removable mounting clip 368 and an outer surface of housing 367, or by any other known holding mechanism. After the iris scan authenticates the prospective user, removable mounting clip 368 may be removed, or slid/rotated aside, allowing the entire display screen to be used for other purposes.

Similarly, a mounting clip may alternatively be used to temporarily mount a beam-spreader and optics train on an existing controllable LED integrated into the housing of the parent device.

FIGS. 4A-H conceptually illustrate examples of beam-shaping elements that may be used in some embodiments of alignment target generators. The examples are non-limiting; other types of beam-shaping elements besides these may be used with embodiments of alignment target generators. Additionally, any of the transmissive elements pictured as examples may be replaced by reflective elements that similarly shape an incident light beam. Some embodiments may include negative-powered beam-shaping elements.

Figure 4A:
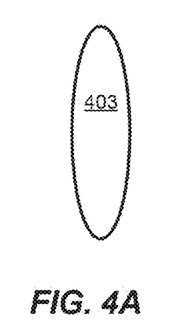
FIGS. 4A-H conceptually illustrate examples of beam-shaping elements that may be used in some embodiments of alignment target generators FIGS. 5A-B conceptually illustrate examples of an annular aperture and an alignment target generator including an annular aperture.

FIG. 4A is a schematic symbol for a planar light source 302 emitting light 310. This symbol in later drawings may represent any of the other illustrated planar light sources or any suitable known substitute.

Figure 4B:
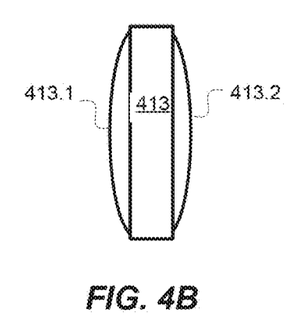

FIG. 4B represents a lens 413 with opposing curvatures 413.1 and 413.2 on two optical surfaces.

Figure 4C:
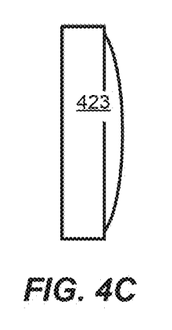

FIG. 4C represents a lens 423 with one planar optical surface and one curved optical surface.

Figure 4D:
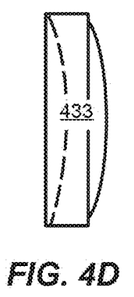

FIG. 4D represents a lens 433 with curves of different radii in the same direction on two optical surfaces.

Figure 4E:
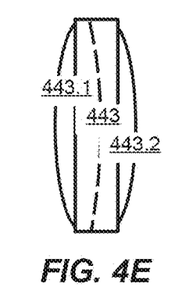

FIG. 4E represents a lens 443 with two elements 443.1 and 443.2 of different materials, e.g., to achromatize a multi-wavelength beam train, or to otherwise differently shape beams of different wavelengths.

Figure 4F:
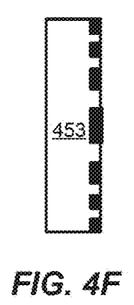

FIG. 4F represents a diffractive (Fresnel) lens 453 with amplitude-modulated transmission.

Figure 4G:
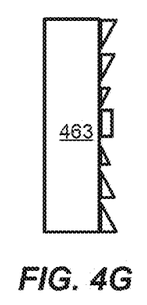

FIG. 4G represents a diffractive (Fresnel) lens 463 with phase-modulated transmission.

Figure 4H:
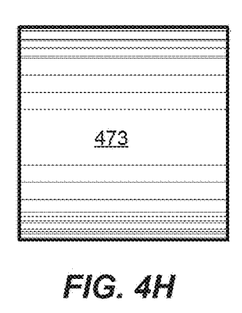

FIG. 4H represents a gradient-index lens 473, which shapes incoming beams with transverse variations in refractive index rather than (or besides) curved or diffraction-patterned optical input or output surfaces.

Figure 5A:
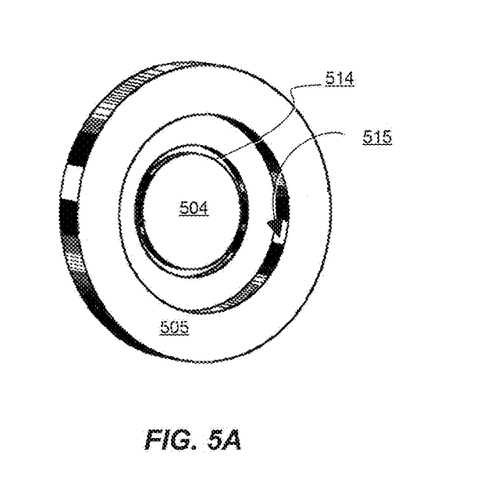
Figure 5B:
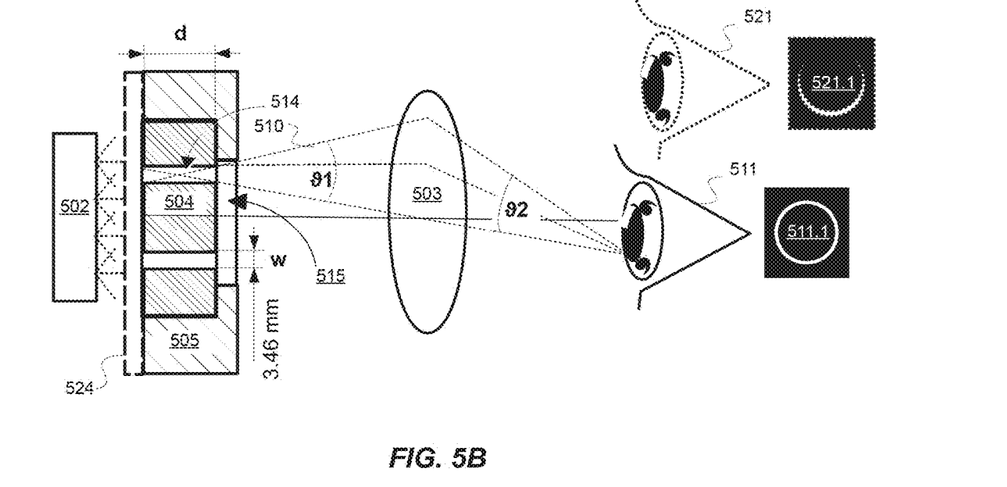

FIGS. 5A-B conceptually illustrate examples of an annular aperture and an alignment target generator including an annular aperture.

In FIG. 5A, beam blocker 504 mounted in housing 505 has a transmissive annular aperture 514 to allow some light to pass through. In the case of a continuous annulus like the one illustrated, the inner and outer parts of beam blocker 504 may be affixed to, or fabricated on, a backplate of material such as glass or plastic that transmits at least some visible light.

Equivalent designs include segmented annuli formed by a number of unconnected holes or arc-shaped slots, including at least three holes or arc-shaped slots equally spaced around the perimeter of the annulus, forming a ring of dots rather than a solid ring. Because the beam-blocker is one piece in such embodiments, a backplate may not be needed for the purpose of maintaining the structure of beam blocker 504.

In FIG. 5B, a cut-away side view of an alignment target generator, planar light source 502 illuminates beam blocker 504, optionally through window or diffuser 524. Window or diffuser 524 may serve as a backplate for beam blocker 504. Light 510 from planar light source 502 exits the annular space or perimeter holes 514 in beam blocker 504. Beam-shaping element 503 captures light 510 and shapes it to form an image of annular space or perimeter holes 514 in beam blocker 504. Aligned eye 511 sees a ring 511.1 (or analogous ring of equally sized dots) with uniform width all around its perimeter. Misaligned eye 521 sees a crescent 521.1 (or analogous crescent of unequally sized dots).

If parts of housing 505 do not vignette light 510 exiting the aperture(s) in beam blocker 504, the alignment sensitivity is determined by the exit angle $\theta 1$, which depends on the depth d (deeper is more sensitive) and width w (wider is less sensitive) of aperture or hole 514, and also by imaging angle $\theta 2$, which depends on the position and focal length of beam-shaping element 503. Similar relationships apply to some other embodiments.

Figure 6A:
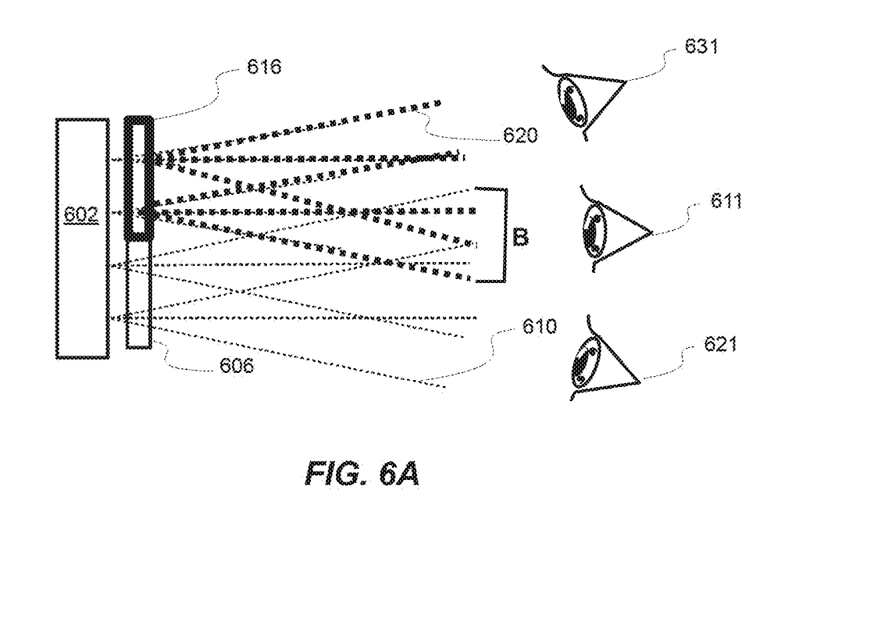
FIGS. 6A-C conceptually illustrate examples of an alignment target generator including one or more color filters that change the color of the planar light source depending on the position and angle of the eye FIGS. 7A-B conceptually illustrate examples of an alignment target generator including a beam blocker pierced by two or more converging waveguides.
Figure 6B:
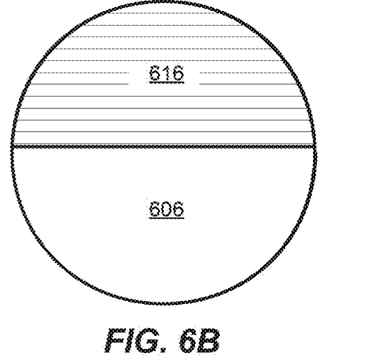
Figure 6C:
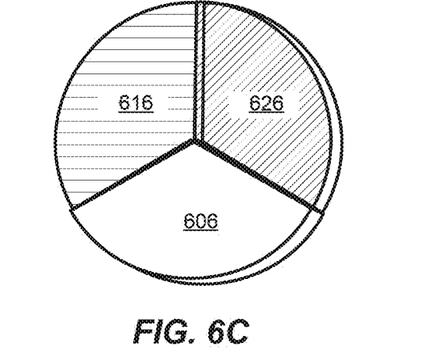

FIGS. 6A-C conceptually illustrate examples of an alignment target generator including one or more color filters that change the color of the planar light source depending on the position and angle of the eye.

In FIG. 6A, a side view of an alignment target generator, planar light source 602 illuminates a window with a spectral response that varies across its width. In this figure, line thickness is used as a proxy for color. As illustrated, bottom window section 606 is substantially clear, transmitting light 610 from planar light source 602 essentially unchanged in color. Top window section 616 is a color filter (absorption or reflection) transmitting colored light 620, a spectral subset of light 610 from planar light source 602.

Aligned eye 611 will see a blended spectrum B (i.e., if light 610 is white and light 620 is red, aligned eye 611 will see pink). Misaligned eye 621 will see white (only light 610), while misaligned eye 631 will see only red (light 620). The alignment target generator of FIG. 6A aligns the eye in one plane parallel to the optic axis.

In FIGS. 6B and 6C, hatching type is a proxy for color.

FIG. 6B is a front view of a 1-D alignment window, showing clear 180-degree sector 606 and color filter 180-degree sector 616.

FIG. 6C is a front view of a 2-D alignment window, showing clear 120-degree sector 606, first color filter 120-degree sector 616, and second (different) color filter 120-degree sector 626.

Alternatively, a 2-D alignment window may have four 90-degree sectors, each transmitting a different color. In all the described embodiments, the transmission spectra of the different sectors produce unambiguously different colors to the user's eye. In some embodiments, the transmission spectra may overlap less than 30%. In some embodiments, the peak wavelengths of the transmission spectra may be more than 100 nm apart.

Note that some embodiments of alignment windows may use a different color filter in place of clear section 606, so that all the exiting light is altered spectrally in different ways.

Figure 7A:
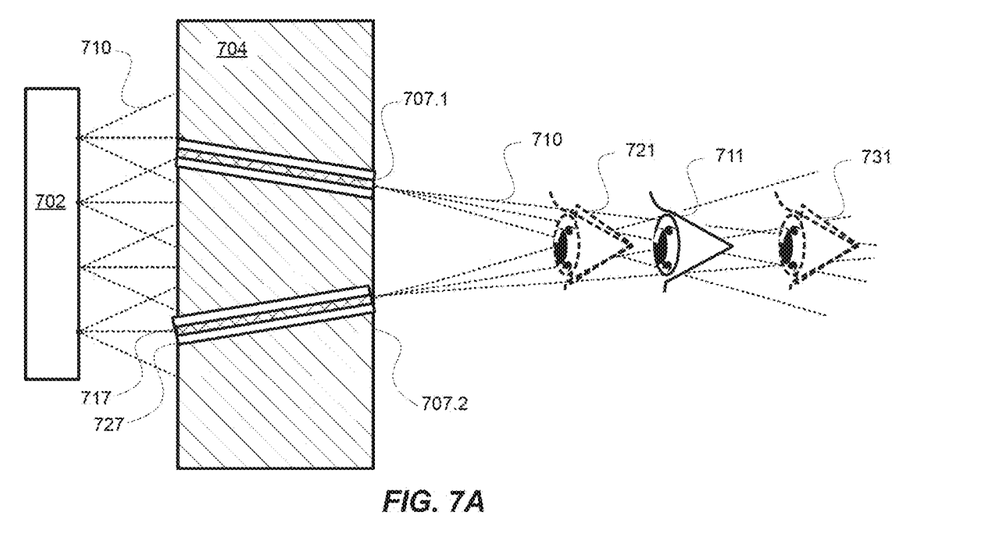
Figure 7B:
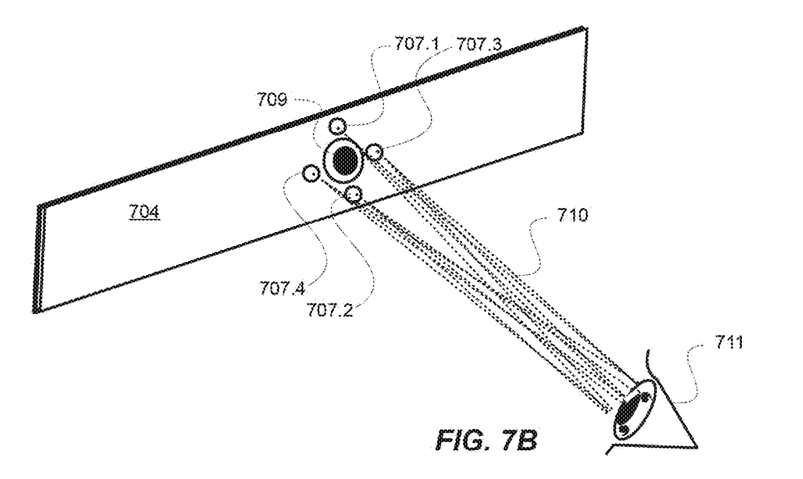

FIGS. 7A-B conceptually illustrate examples of an alignment target generator including a beam blocker pierced by two or more converging waveguides.

In FIG. 7A, a cut-away side view, beam blocker 704 is pierced by waveguides 707.1 and 707.2, which capture and transmit light 710 from planar light source 702. Waveguides 707.1 and 707.2 may be rigid or flexible. Waveguides 707.1 and 707.2 may include transmissive core 717 and lower-index cladding 727.

Light 710 exits waveguides 707.1 and 707.2 at a full angle corresponding to the numerical aperture of the waveguides. Additionally, the optic axes of the exiting cones of light converge with each other. Aligned eye 711 is in the smallest spot created by the convergence of the cones. Misaligned eyes 721 are in larger spots; they may still see two dots, but they will be dimmer and perhaps distorted.

In FIG. 7B, a front perspective view, four waveguides 707.1-4, 90 degrees apart on a circle perimeter, converge to allow alignment in 2 orthogonal axes. 3 waveguides 120 degrees apart would provide non-orthogonal 2-D alignment. In both cases, aligned eye 711 is positioned in the minimum spot for the brightest dots. Scanner input 709 may be located in the center of the circle of waveguide tips. Optionally, beam blocker 704 may be a wall of the parent device's housing.

Figure 8:
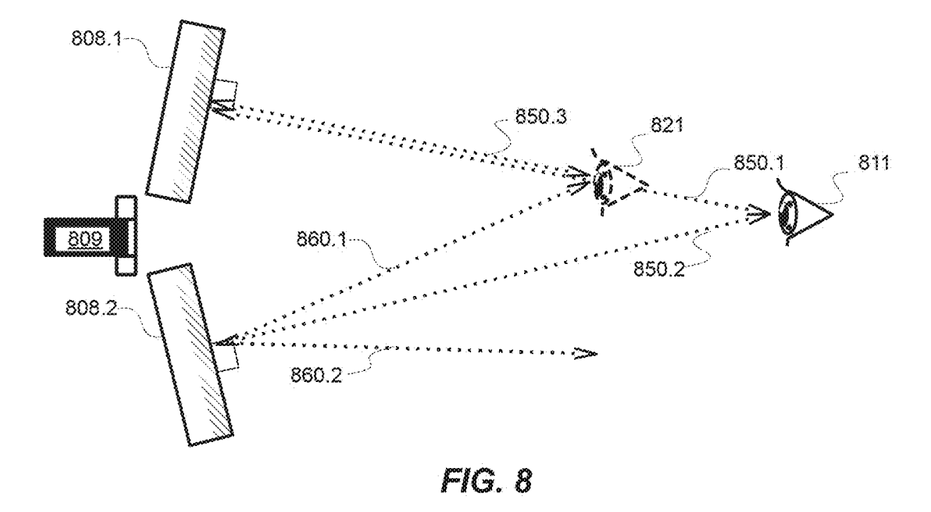
FIG. 8 conceptually illustrates a tilted-mirror alignment target generator.

FIG. 8 conceptually illustrates a tilted-mirror alignment target generator. Mirrors 808.1 and 808.2 are positioned on either side of scanner input 809 and tilted inward toward the scanner input's optic axis along the perimeter of a cylinder centered on aligned eye 811. Planar light sources off-axis (not shown) provide illumination to mirrors 808.1 and 808.2.

Aligned eye 811 sees both mirrors 808.1 and 808.2 because the surfaces of the eye reflect light rays 850.1 and 850.2 back at normal or near-normal angles to the mirrors. Misaligned eye 821 sees mirror 808.1 because the eye reflects ray 850.3 along a normal to mirror 808.1. However, misaligned eye 821 does not see mirror 808.2 because ray 860.1 makes a non-normal angle with mirror 808.2 and is reflected as ray 860.2 away from the eye.

In some embodiments of alignment target generators, the planar light source is blocked or powered down before the biometric measurement begins, to avoid excess reflections that may mask features of the iris.

A 2-D alignment target generator of this type would use at least 3 mirrors arranged around scanner input 809 om the surface of a sphere concentric with the aligned eye position.

Facial recognition scores high in collectability and acceptability (iris scanning's weaker areas) as well as universality, in the midrange of uniqueness and permanence, but low in performance and (difficulty of) circumvention. 2-D face recognition is limited in the head positions and angles at which it can measure without losing accuracy. Some of the described alignment techniques for the eye may also help reduce the error margin in face recognition.

At the same time, remote monitoring of health factors promises to reduce healthcare costs for both patients and healthcare providers. When the nearest doctor's office is far away and reliable transportation is scarce, or when visits to crowded urban clinics are stressful and pose a risk of contagion, routine post-treatment follow-up may sometimes have practical, as well as financial, advantages. Visual views of a patient's eyes or face can be helpful for tracking the development of irritations or infections, the healing of wounds and surgical incisions, or other changes in appearance that may indicate changes in underlying health. However, the information value of a set of serial photographs may be limited if the distance, angle, lighting, and other factors vary widely from picture to picture.

Therefore, the alignment target generators described herein may also be applicable in face recognition and medical communication.

The preceding Description and accompanying Drawings describe examples of embodiments in some detail to aid understanding. However, the scope of protection may also include equivalents, permutations, and combinations that are not explicitly described herein. Only the claims appended here (along with those of parent, child, or divisional patents, if any) define the limits of the protected intellectual-property rights.

We claim:

1. A device, comprising:
    a planar light source; and
    an optical train to transmit or reflect light from the planar light source to an aligned eye position;
    wherein the optical train comprises at least one of: a beam blocker having an annular aperture of uniform width, a window having a plurality of sectors with each sector having a different transmission spectrum, a plurality of waveguides at angles that converge toward the aligned eye position, or a plurality of mirrors tangent to a surface of a sphere concentric with the aligned eye position;
    wherein a characteristic of the transmitted or reflected light that exits the optical train is visible to an aligned eye at the aligned eye position;
    wherein the characteristic is not visible to a misaligned eye at a position that differs from the aligned eye position by more than a threshold; and
    wherein the threshold is defined by a loss or distortion of biometric data compared to that available from a user with an aligned eye.

2. The device of claim 1, wherein the planar light source comprises a light-emitting diode array.

3. The device of claim 1, wherein the planar light source comprises:
    a light-emitting diode; and
    a first optical element positioned to reconfigure emitted light from the light-emitting diode to a form resembling light emitted from a planar source.

4. The device of claim 1, wherein the planar light source comprises a self-illuminating screen.

5. The device of claim 1, wherein the optical train comprises the beam blocker, and further comprises:
    a beam-shaping element forming an image of the annular aperture;
    wherein the aligned eye sees an illuminated annulus of uniform width; and
    wherein the misaligned eye sees an illuminated crescent.

6. The device of claim 1, wherein the optical train comprises the window having a plurality of sectors, and:
    the window has a first transmission spectrum in a first 180-degree sector and a second transmission spectrum in a second 180-degree sector;
    wherein the aligned eye sees a color corresponding to the planar light source filtered by an average of the first transmission spectrum and the second transmission spectrum; and
    wherein the misaligned eye sees a color corresponding to the planar light source filtered by the first transmission spectrum or the second transmission spectrum.

7. The device of claim 1, wherein the optical train comprises the window having a plurality of sectors, and:
    the window has a first transmission spectrum in a first 120-degree sector, a second transmission spectrum in a second 120-degree sector, and a third transmission spectrum in a third 120-degree sector;
    wherein the aligned eye sees a color corresponding to the planar light source filtered by an average of the first transmission spectrum, the second transmission spectrum, and the third transmission spectrum; and
    wherein the misaligned eye sees a color corresponding to the planar light source filtered by the first transmission spectrum, the second transmission spectrum, or the third transmission spectrum.

8. The device of claim 1, wherein the optical train comprises a beam blocker pierced by the plurality of waveguides at angles that converge toward the aligned eye position;
    wherein light from the planar light source enters and exits each of the waveguides;
    wherein the aligned eye sees a maximally bright dot corresponding to each waveguide; and
    wherein the misaligned eye sees dimmer or fewer dots.

9. The device of claim 1, wherein the optical train comprises the plurality of mirrors tangent to the surface of a sphere concentric with the aligned eye position;
    wherein the aligned eye sees all of the plurality of mirrors; and
    wherein the misaligned eye sees fewer than all of the plurality of mirrors.

* * * * *